US005567617A

United States Patent [19]

Caprio et al.

[11] Patent Number: 5,567,617

[45] Date of Patent: Oct. 22, 1996

[54] APPARATUS FOR HEATING A FLUID-CARRYING COMPARTMENT OF REACTION CUVETTE

[75] Inventors: Craig A. Caprio; Michael R. Van der Gaag, both of Rochester, N.Y.; Charles C. Hinckley, Santa Rosa, Calif.; John B. Chemelli, Webster, N.Y.

[73] Assignee: Johnson & Johnson Clinical Diagnostics, Inc., Rochester, N.Y.

[21] Appl. No.: 369,057

[22] Filed: Jan. 5, 1995

Related U.S. Application Data

[63] Continuation-in-part of Ser. No. 178,206, Jan. 6, 1994, abandoned.

[51] Int. Cl.$^{6}$ .............................. C12M 1/40; C12M 1/38

[52] U.S. Cl. .............................. 435/287.2; 435/288.7; 435/303.1

[58] Field of Search .............................. 435/290, 316, 435/869, 291, 288, 6, 287.2, 287.3, 288.7, 303.1; 422/104, 99; 165/61, 86; 291/200, 201, 443; 436/174

[56] References Cited

U.S. PATENT DOCUMENTS

| | | | |
|---|---|---|---|
| 3,346,440 | 10/1967 | Kruger | 156/583 |
| 3,450,031 | 6/1969 | Peterson | 100/93 |
| 3,480,015 | 11/1969 | Gonzalez | 128/276 |
| 3,567,560 | 3/1971 | Stiff | 156/583 |
| 3,586,820 | 6/1971 | Yamanaka | 219/222 |
| 3,590,215 | 6/1971 | Anderson et al. | 219/298 |
| 3,645,066 | 2/1972 | Drygulski | 53/112 A |
| 3,898,427 | 8/1975 | Levin et al. | 219/522 |
| 3,923,590 | 12/1975 | Humphries | 156/580 |
| 3,979,248 | 9/1976 | Kussmaul | 156/358 |
| 3,988,981 | 11/1976 | McDonald | 100/99 |
| 4,038,030 | 7/1977 | Albright et al. | 23/230 |
| 4,163,896 | 8/1979 | McAvinn et al. | 219/525 |
| 4,165,456 | 8/1979 | Dogliotti | 219/449 |
| 4,172,750 | 10/1979 | Giulie | 156/267 |
| 4,190,485 | 2/1980 | Takeda et al. | 156/583.9 |
| 4,210,798 | 7/1980 | Ode et al. | 219/243 |
| 4,317,697 | 3/1982 | McLean | 156/583.1 |
| 4,384,193 | 5/1983 | Kledzik et al. | 435/809 |
| 4,386,993 | 6/1983 | Matsuo | 156/358 |
| 4,408,520 | 10/1983 | Wons et al. | 100/93 |
| 4,479,844 | 10/1984 | Yamada | 156/583.2 |
| 4,612,081 | 9/1986 | Kasper et al. | 156/583.1 |
| 4,624,730 | 11/1986 | Reyer et al. | 156/358 |
| 4,645,559 | 2/1987 | Kaiser et al. | 156/583.1 |
| 4,661,683 | 4/1987 | Glucksman | 219/222 |
| 4,701,293 | 10/1987 | Mead | 264/258 |
| 4,794,224 | 12/1988 | Spektor et al. | 219/216 |
| 4,906,816 | 3/1990 | van Leerdam | 219/299 |
| 4,970,376 | 11/1990 | Mellor et al. | 219/543 |
| 5,089,233 | 2/1992 | DeVaney, Jr. et al. | 422/99 |
| 5,095,813 | 3/1992 | Escamilla et al. | 99/349 |
| 5,098,660 | 3/1992 | Devaney, Jr. | 422/99 |
| 5,119,467 | 6/1992 | Barsky et al. | 392/439 |
| 5,140,136 | 8/1992 | Fellows et al. | 219/521 |
| 5,143,694 | 9/1992 | Schafer et al. | 422/65 |
| 5,167,750 | 12/1992 | Myers | 156/583.9 |
| 5,171,970 | 12/1992 | Chichlowski et al. | 219/243 |
| 5,241,415 | 8/1993 | Argentieri et al. | 359/395 |
| 5,281,516 | 1/1994 | Stapleton et al. | 435/809 |
| 5,346,672 | 9/1994 | Stapleton et al. | 435/290 |

FOREIGN PATENT DOCUMENTS

| | | | |
|---|---|---|---|
| 0381501 | 8/1990 | European Pat. Off. | B01L 3/00 |
| 93 19207 | 9/1993 | WIPO . | |

*Primary Examiner*—William Beisner
*Attorney, Agent, or Firm*—Dana M. Schmidt

[57] ABSTRACT

A heating assembly useful in apparatus for processing reaction cuvettes for replicating specified DNA sequences, such as those using PCR, having a heating element with a heat delivering surface for compressively contacting a pliable fluid-carrying compartment of a supported cuvette. The heat delivering surface has a defined passage sized to allow the detection compartment to be situated therein so that the compartment can be efficiently heated. Fluid flow through the compartment, however, is not interfered with during the heating process due to the presence of the defined passage. In addition, the heat delivering surface can be made from optically transparent materials so that visual detection within the processor can take place.

15 Claims, 9 Drawing Sheets

APPARATUS FOR HEATING A FLUID-CARRYING COMPARTMENT OF REACTION CUVETTE

CROSS-REFERENCE TO RELATED APPLICATIONS

This is a continuation-in-part application of U.S. Ser. No. 178,206, filed on Jan. 6, 1994, entitled "Apparatus For Heating A Fluid-Carrying Compartment", now abandoned.

BACKGROUND OF THE INVENTION

The invention is directed to apparatus for the processing of reaction cuvettes, such as for amplification and detection of specific nucleic acid sequences, and in particular to the mounting of heating assemblies to heat by contact a fluid-carrying compartment of such cuvettes.

Self contained reaction cuvettes are known and described, such as in EPA Publication No. 0/381,501, in which amplification of specified nucleic acids, such as a DNA sequence(s) can take place by means of polymerase chain reaction technology (hereinafter PCR). The cuvettes are self-contained such that a sample can be introduced within its confines, the cuvettes having separate reaction, reagent and detection compartments so that amplification, wash and detection can be performed. The individual compartments of the reaction cuvette are preferably thin walled and made from a pliable material which is preferably transparent. Within the detection compartment of a typical reaction cuvette, controls or other detection means are located within or added to the pliable, see-through compartment.

In order to effectively conduct the amplification process, including the detection of replicated nucleic acid, such as DNA, it is important to heat the detection compartment as well as other portions of the cuvette. Efficient heating, such as by conduction, requires that heating elements be placed in direct compressive contact with the reaction cuvette. It is also essential, however, that fluid communication into and out of the detection compartment is not constricted so that liquid will be able to contact the detection controls located therein, as well as having the ability to flow out into adjacent compartments, such as for the collection of waste products.

Therefore, there is a need to provide a heating assembly which will effectively heat by contact a fluid-carrying compartment of a reaction cuvette, such as those described, while also allowing fluid flow to proceed through the compartment.

SUMMARY OF THE INVENTION

The present invention solves the above stated needs by providing an assembly comprising a first heating element for heating a fluid-carrying compartment by contact, the element having a source of heat as well as a heat-delivering surface which is characterized by means defining a passage which is sized to receive the fluid-carrying compartment, and which allows the heating element to be placed into contact with said reaction cuvette so as to heat the compartment by intimate thermal contact but without restricting fluid flow therethrough, the reaction cuvette being supported by support means.

According to another aspect of the present invention, there is disclosed a processing apparatus comprising a main body having means for defining an interior portion, a cover movably coupled to said main body, a support disposed within said interior portion for supporting a reaction cuvette, a first heating element for heating by contact a portion of said reaction cuvette comprising at least one fluid-carrying compartment made from a compliant material, the first heating element being characterized by means defining a passage sized to receive a fluid-carrying portion of the cuvette to permit fluid flow therethrough while the first heating element is in contact with the cuvette.

According to yet another aspect of the invention, there is provided a method of processing a cuvette with a flexible detection compartment to detect nucleic acid targets, by heating the compartment between heating surfaces, the compartment being defined by flexible walls, the method comprising the steps of a) disposing the cuvette between heating surfaces that are spaced apart around the compartment a fixed distance, one of the surfaces having a viewing window through which the compartment extends, so that the heating surfaces constrain the walls of the compartment to a predetermined maximum expansion, b) forcing fluid carrying any target nucleic acid to flow through the detection compartment at while the walls are expanded to the maximum expansion while heating the surfaces, and c) thereafter, forcing detection reagents to flow through the detection compartment at the maximum expansion, while heating the surface.

An advantageous feature realized by the present invention is that a reaction cuvette, useful for nucleic acid amplification, can be placed within a processor so that a detection compartment of the cuvette can be brought into intimate thermal contact with the heat delivering surface so as to promote efficient heating of the compartment, while still permitting fluid flow to proceed into and out of the compartment.

Another advantageous feature of a processor having the heating assembly according to the present invention is that the results of the reaction can be observed without having to open the processor, and without having to interfere with the amplification or detection aspects of the process.

Other advantageous features will become apparent upon reference to the following Description of the Preferred Embodiments, when read in light of the attached drawings.

DETAILED DESCRIPTION OF THE PREFERRED EMBODIMENTS

The invention is hereinafter described in the context of the preferred embodiments.

Terms such as "up", "down", "lower", "vertical", "horizontal", and "bottom" as used herein refer to the orientation of parts when the apparatus is positioned in its customary position of use.

Figure 1:
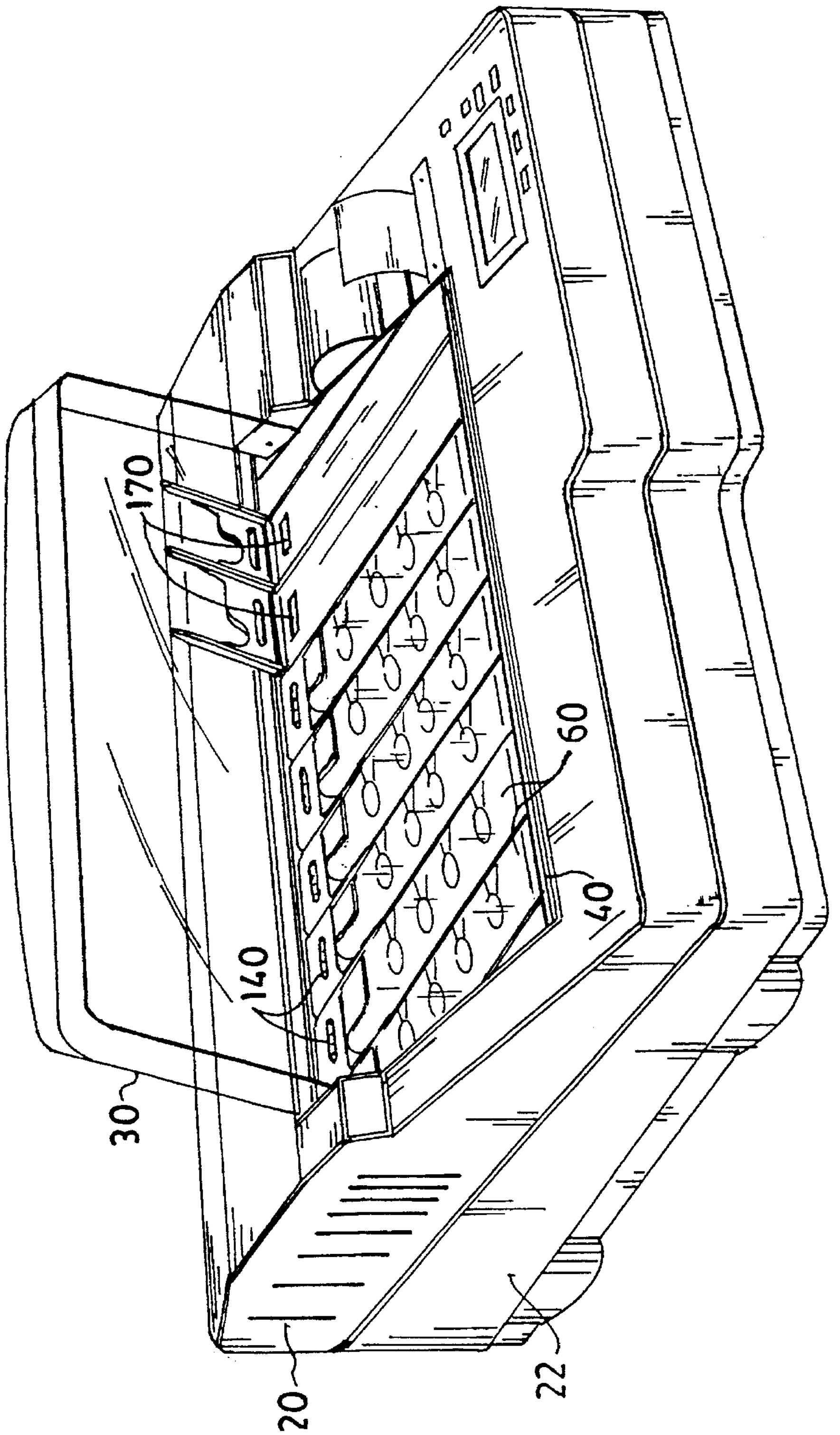
FIG. 1 is a frontal perspective view of a processing apparatus according to one embodiment of the present invention.

Referring to FIG. 1, there is provided a processor 20 for performing DNA replication through the use of PCR (polymerase chain reaction) technology of a plurality of reaction cuvettes 60, the apparatus having a cover 30, a movable support plate 40 for supporting the plurality of reaction cuvettes 60, and upper and lower heating assemblies 140, 170, for heating a fluid-carrying portion of each supported cuvette 60.

Figure 2:
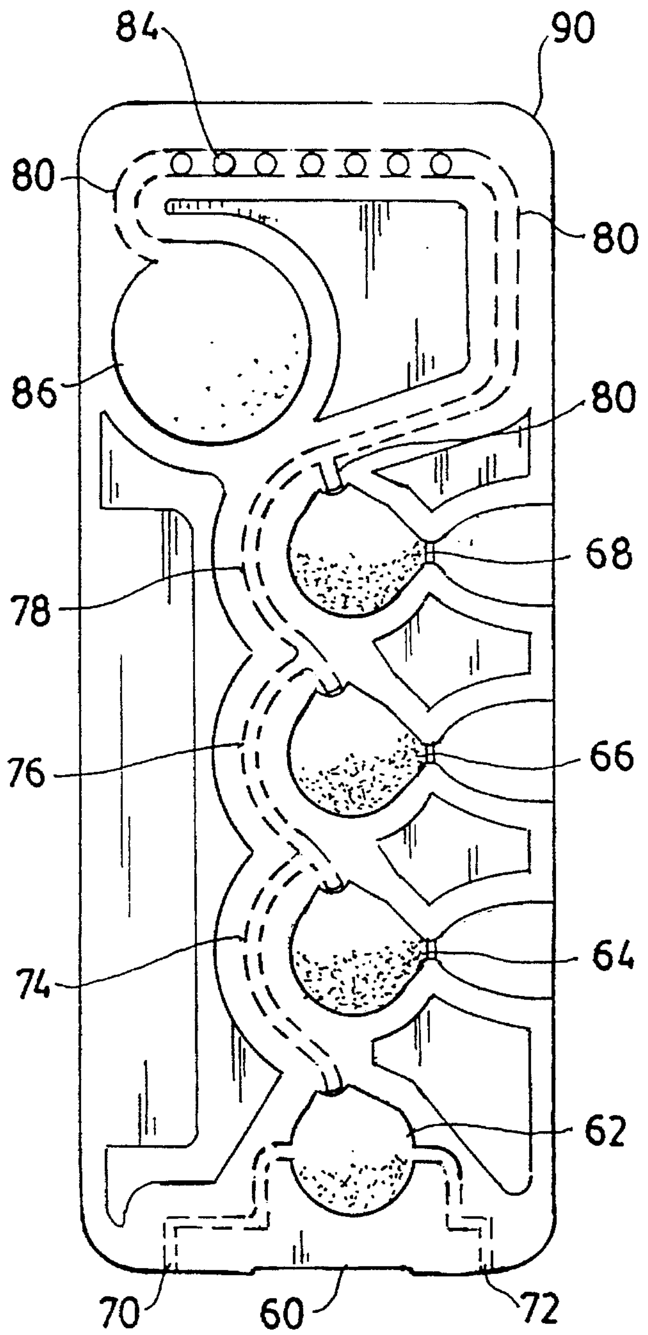
FIG. 2 is a top plan view of a reaction cuvette which is useful in the processor shown in FIG. 1.

Prior to a detailed discussion of the general workings of processor 20, and in particular heating assemblies 140, 170, it is important to understand the structure and operation of a typical PCR reaction cuvette 60. A particular configuration of a reaction cuvette 60 is illustrated in FIG. 2. Cuvette 60 is defined as a self-contained pouch having a reaction compartment 62 and adjacent storage compartments 64, 66, 68. Inlet means 70, 72 allow a sample and reagents for promoting the amplification process to be added to reaction chamber 62, though the reagents could already be preincorporated therein. All of the compartments are interconnected by a network of flow passageways 74, 76, 78, 80 which lead sequentially to a detection compartment 84. Flow passageway 80 extends from the other side of detection compartment 84 to a waste chamber 86.

As noted previously, the entire cuvette 60 is self-contained and is formed by heat-sealing two thin-walled plastic sheets 88, 90 together at their respective side edges. Details of the manufacture of the described cuvettes are described in EPA Publication No. 0/550,090 which is hereby incorporated by reference.

Nucleic acid amplification, in general, is done by the introduction of sample into reaction compartment 62 via inlet means 70, 72 into which reagents are also added, or are already preincorporated. These inlet means 70, 72 are then permanently closed off to preserve the self-contained nature of the cuvette. Typically, the inlet means are heat-sealed after introduction of sample. These reagents, in combination with thermal cycling of reaction compartment 62 allow denaturing of the DNA or other nucleic acid strands and subsequent replication to produce amplified nucleic acid. Once the desired amount of nucleic acid material has been produced within chamber 62, external pressure can then be applied to force the contents of chamber 62 along flow passageway 74 and towards detection compartment 84. Sequentially, the pressurizing of adjacent storage compartments 64, 66, 68, according to a particular protocol, force wash liquid and detection reagents from their respective compartments to traverse flow passageways 76, 78 and 80 so that their contents may be added to detection compartment 84 which already contains means for immobilizing amplified nucleic acid for detection therein. Excess liquid is forced from detection compartment 84 to adjacent waste compartment 86. With the possible exception of the introduction of sample the entire process, including detection, can be completed without having to open cuvette 60, thereby avoiding aerosoling problems which could contaminate a laboratory environment. Details of the processing of cuvettes 60, including detection, can be found in EPA Publication No. 0/381,501, which is also hereby incorporated by reference.

Figure 3:
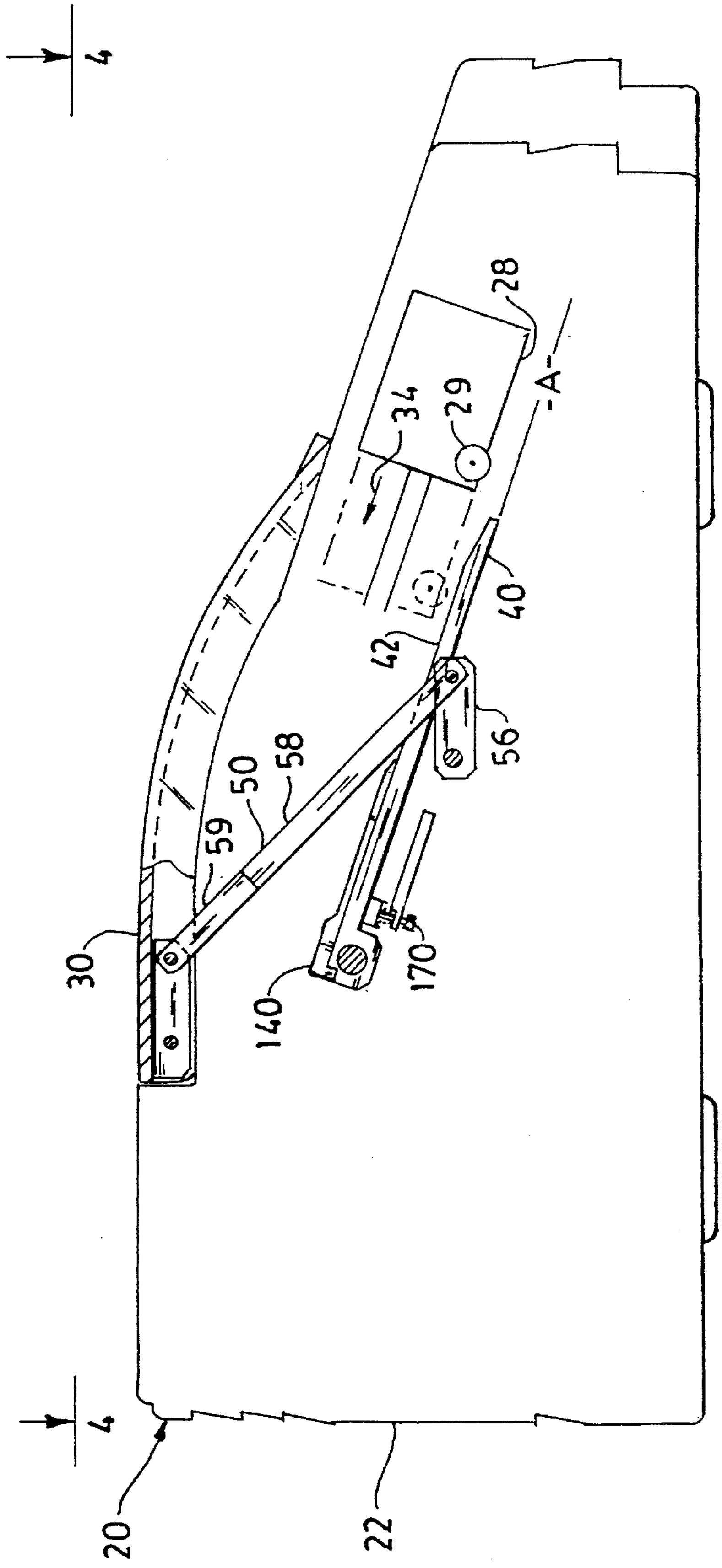
FIG. 3 is a fragmented side elevational view, partially sectioned, of the processor shown in FIG. 1, particularly showing the relationship between the cover of the processor and a support plate located therein.
Figure 4:
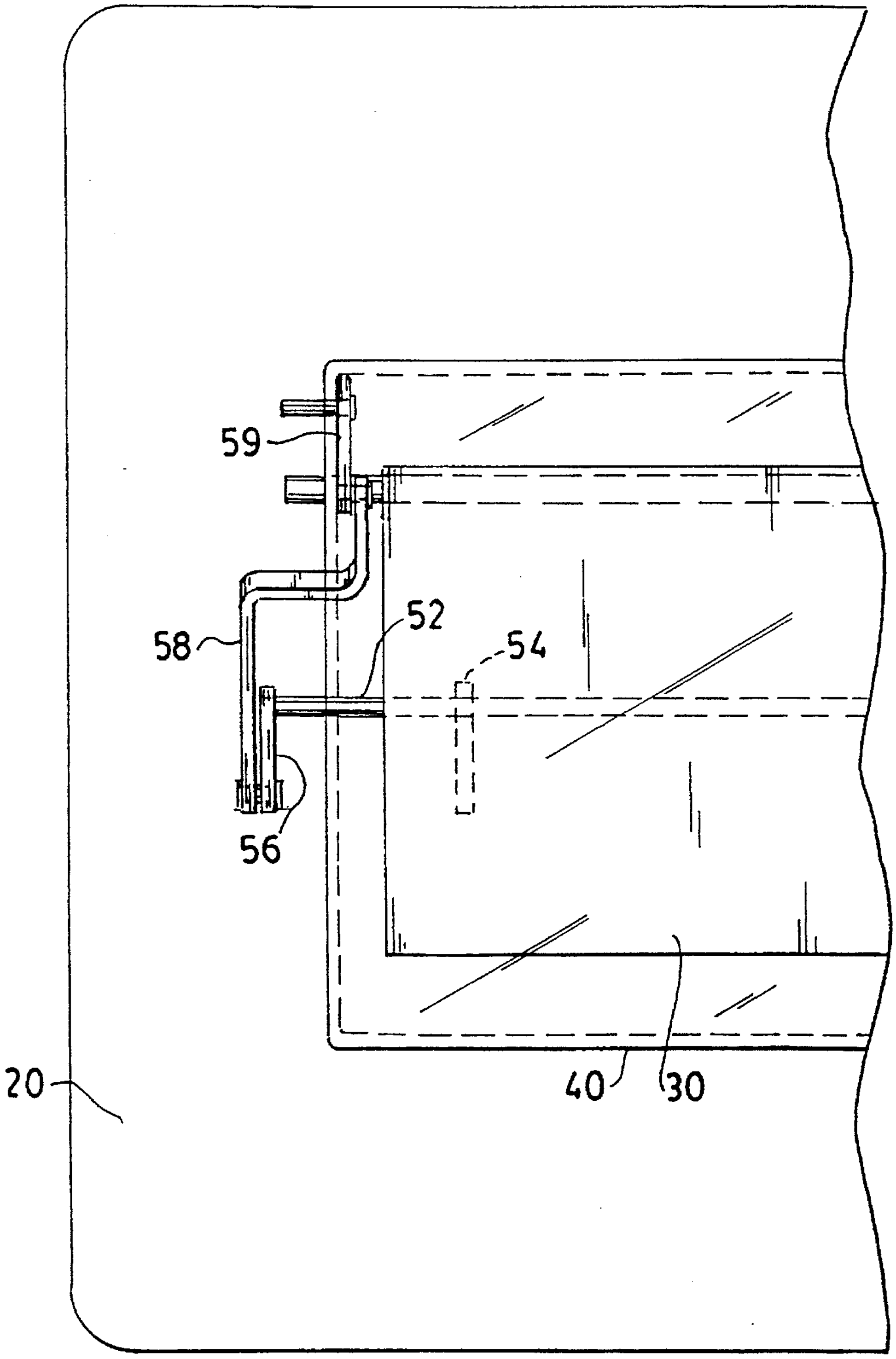
FIG. 4 is a partial top plan view of the processor of FIG. 3.
Figure 5:
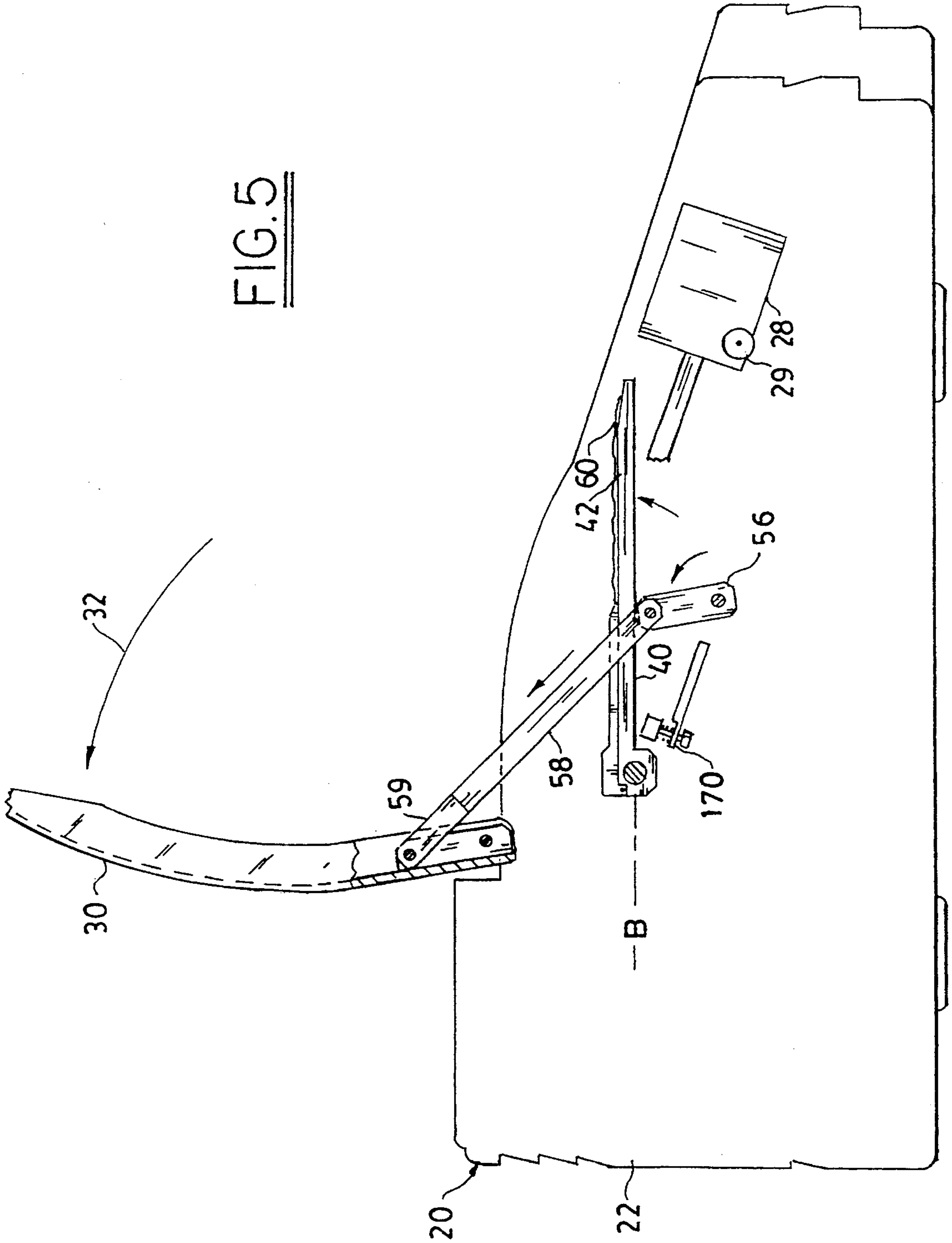
FIG. 5 is a fragmented side elevational view, partially shown in section, of the processor of FIGS. 3 and 4.

Referring to FIGS. 3–5, the general workings of processor 20 will now be described. Cover 30 is movably attached to the main body 22 of processor 20 so that it can open and close as per arrow 32, FIG. 5, thereby allowing operator access to an interior portion, for loading and unloading of cuvettes 60. Preferably, cover 30 is made from a lightweight, transparent material to allow user viewing. In the embodiment illustrated, cover 30 is made from polycarbonate, and main body 22 is made of polycarbonate, though other conventional structural materials, such as polyesters, polyamides, polyurethanes, polyolefins, polyacetals, phenolformaldehyde resins, etc., can be used.

Disposed within the interior portion is a support plate 40, sized to receive at least one PCR pouch or cuvette 60 of the type previously described above. In the embodiment illustrated, support plate 40 is sized to hold a plurality of reaction cuvettes 60 to be placed along a top surface 42, the cuvettes 60 being generally parallel and equally spaced apart with respect to one another when they are loaded. When cover 30 is closed, support plate 40 is initially in an inclined first position (A). When cover 30 is closed, as in the embodiment illustrated, support plate 40 is inclined approximately 19 degrees from horizontal, FIG. 3. The specified angle of inclination of position (A), however, is not critical to the operation of the present invention, but is preferable for ease of loading and unloading of cuvettes 60, as is discussed in greater detail below.

Support plate 40 is movably attached to cover 30 by camming means comprising a rotatable cam shaft 52 having a plurality of cam surfaces 54 extending therefrom, shaft 52 being positioned beneath support plate 40. Shaft 52 is connected at one end along one side of processor 20 by a movable lower linkage 56 which is pinned or otherwise attached to a pivot arm 58 extending to an upper linkage 59 which is connected to one side of cover 30. A set of bearings (not shown) enables smooth, repeatable rotation of cam shaft 52.

The operation of camming means 50 can be seen by also referring to FIGS. 3–5. As cover 30 is opened, FIG. 5, per arrow 32, cam shaft 52 is rotated in a counterclockwise fashion, as shown, thereby engaging cam surfaces 54, FIG. 4, against the bottom of support plate 40, and relocating support plate 40 to substantially horizontal position (B) in which reaction cuvettes 60, FIG. 2, as previously described, can more easily be loaded. In like manner, when cover 30 is closed, cam shaft 52 reverses direction and returns support plate 40 to initial position (A), FIG. 3. In a preferential embodiment, an extension spring (not shown) can be added to cover 30 which is loaded upon opening and provides uniformity in registering cam surfaces 54 when cover 30 is closed.

Processor 20 is also provided with a translatable roller arm 28 which can be engaged per arrow 34 against support plate top surface 42. Roller arm 28 is guided by control means, such as a microprocessor (not shown), and is driven by a servo motor and a belt mechanism (not shown) to engage a loaded cuvette 60, FIG. 2, by means of a series of retractable rollers 29 extending from the bottom surface of roller arm 28 for compressing sequentially the reaction compartment 62 and storage compartments 64, 66, 68 of a plurality of loaded cuvettes.

It can be seen that roller arm 28 can freely move along top surface 42 when support plate 40 is in position (A), FIG. 3, but is not free to engage support plate when cuvettes are being loaded in position (B), FIG. 5.

Figure 6:
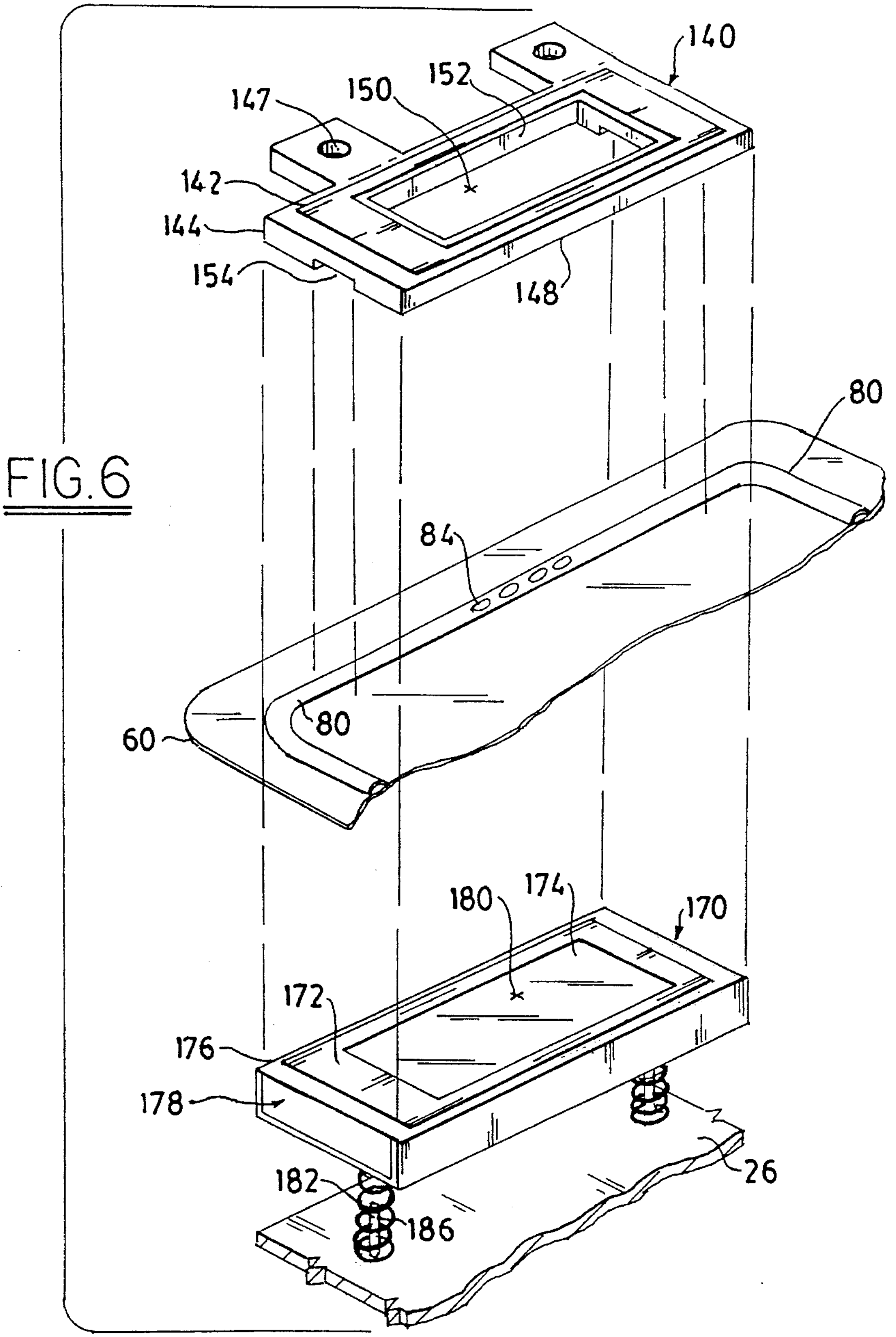
FIG. 6 is an exploded perspective view of portions of an upper and lower heating assembly according to the present invention in relation to the reaction cuvette of FIG. 2.

Referring to FIGS. 1 and 6, an upper and lower detection heater assembly 140 and 170, respectively are each provided for engaging the detection compartment 84 and flow passageways 80 of a reaction cuvette 60.

Upper heater assembly 140 comprises a first heating element 142, such as a thin electrically resistive member, which is bonded to one side of an aluminum or other thermally conductive support or mount fixture 144. Heating element 142 is further preferably defined by a peripheral configuration about a through aperture 150 provided in mount fixture 144, and sized to receive the detection compartment 84 of a reaction cuvette 60, when aligned according to FIG. 6. Aperture 150 cooperates with transparent processor cover 30 to permit visual inspection of detection compartment 84 without interfering with the heating thereof.

Due to the thermally conductive nature of mount fixture 144, heat can be transmitted through inner sidewalls 152, as well as through lower surface 148, thereby defining a first heat delivering surface for assembly 140 to heat by contact a reaction cuvette 60.

Lower surface 148 is further defined by a channel or passage 154, preferably sized to receive flow passageway 80 on either side of detection compartment 84. Channel 154 extends across the length of heat-delivering surface 148, except for aperture 150, and provides for a recessed area whereby any downward compressive force exerted by mount fixture 144 is transmitted by the remainder of lower surface 148, to portions of the surface area of cuvette 60, but not to the fluid-carrying portions defined by detection compartment 84 and flow passageways 80.

Still referring to FIG. 6, a second or lower heating assembly 170 is provided for contacting the underside of reaction cuvette 60 in the vicinity of detection compartment 84. Lower heating assembly 170 comprises a second heating element 172, such as an electrically resistive member which is bonded to an exterior surface of a glass, or preferably other optically transparent member 174, such as sapphire. A holding fixture or button 176, retains glass member 174 and heating element 172 in a holding aperture 178, sized so that glass member 174 is fully contained therein, preferably such that the exterior surface of glass member 174 is substantially flush with the open periphery of button 176.

Figure 7:
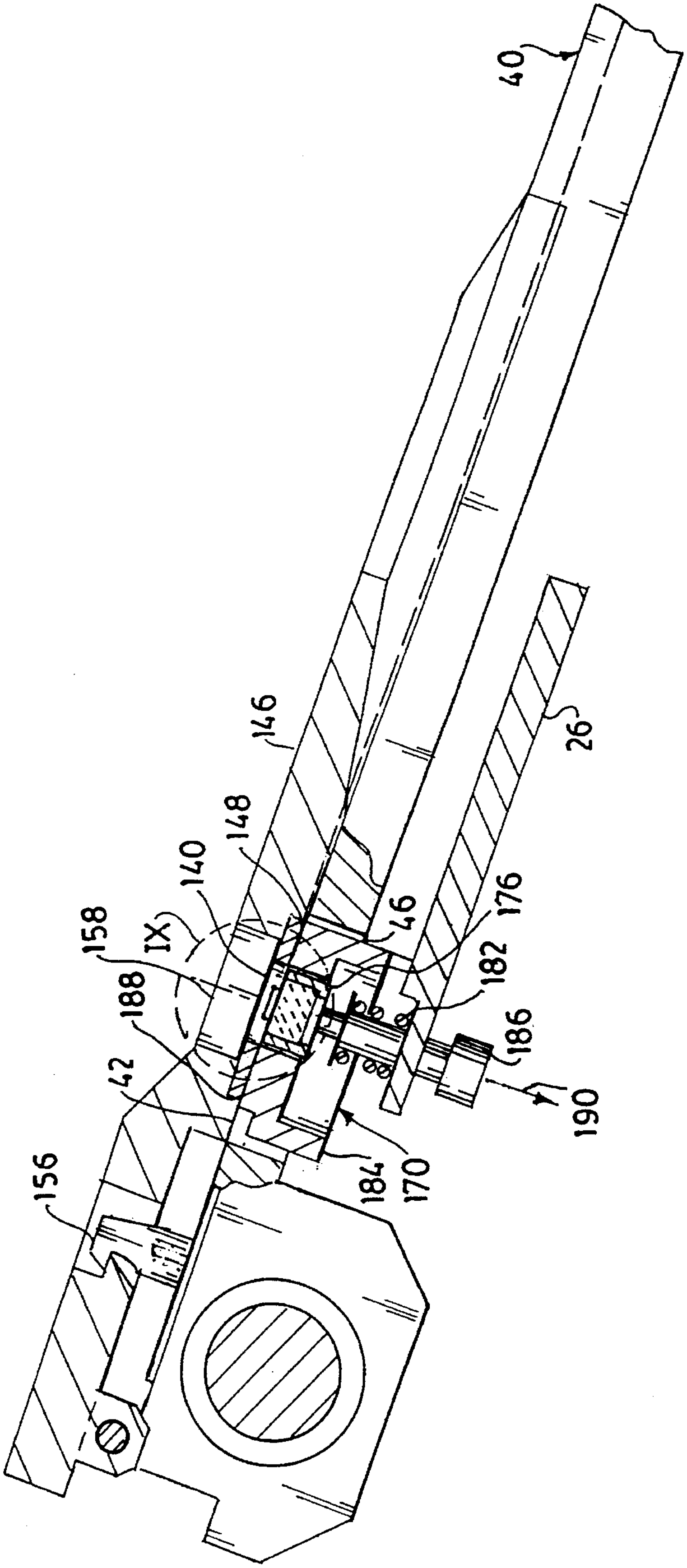
FIG. 7 is a partial side elevational view of the processor of FIG. 1, shown in section, illustrating the engagement of the heating assemblies of FIG. 6 while the cover of the processor is closed.

A pair of compression springs 182 are provided between the bottom surface of button 176 and a stationary weldment 26, of processor 20 which is located beneath support plate 40, FIG. 7, and which spans the interior portion of processor 20, springs 182 being supported via a set of shoulder screws 186. It can be seen from FIGS. 3, 5 that as support plate 40 is made to move from position (A) to position (B), lower heating assembly 170 essentially remains fixed.

Thin heating element 172 is defined by a similar peripheral edge configuration as upper assembly 140 to enclose a substantially central see-through portion, or window 180 of glass member 174 which is sized to fit detection compartment 84. A similar window (not shown) is provided along the bottom surface of button 176 to permit an optical path for detection compartment 84, such as by machine means (not shown).

In the embodiment illustrated, a series of second heating assemblies 170 are provided in processor 20. Sources of heat necessary to engage heating elements 142, 172, such as a resistive coil, are not shown, but such heat sources are commonly known.

Figure 8:
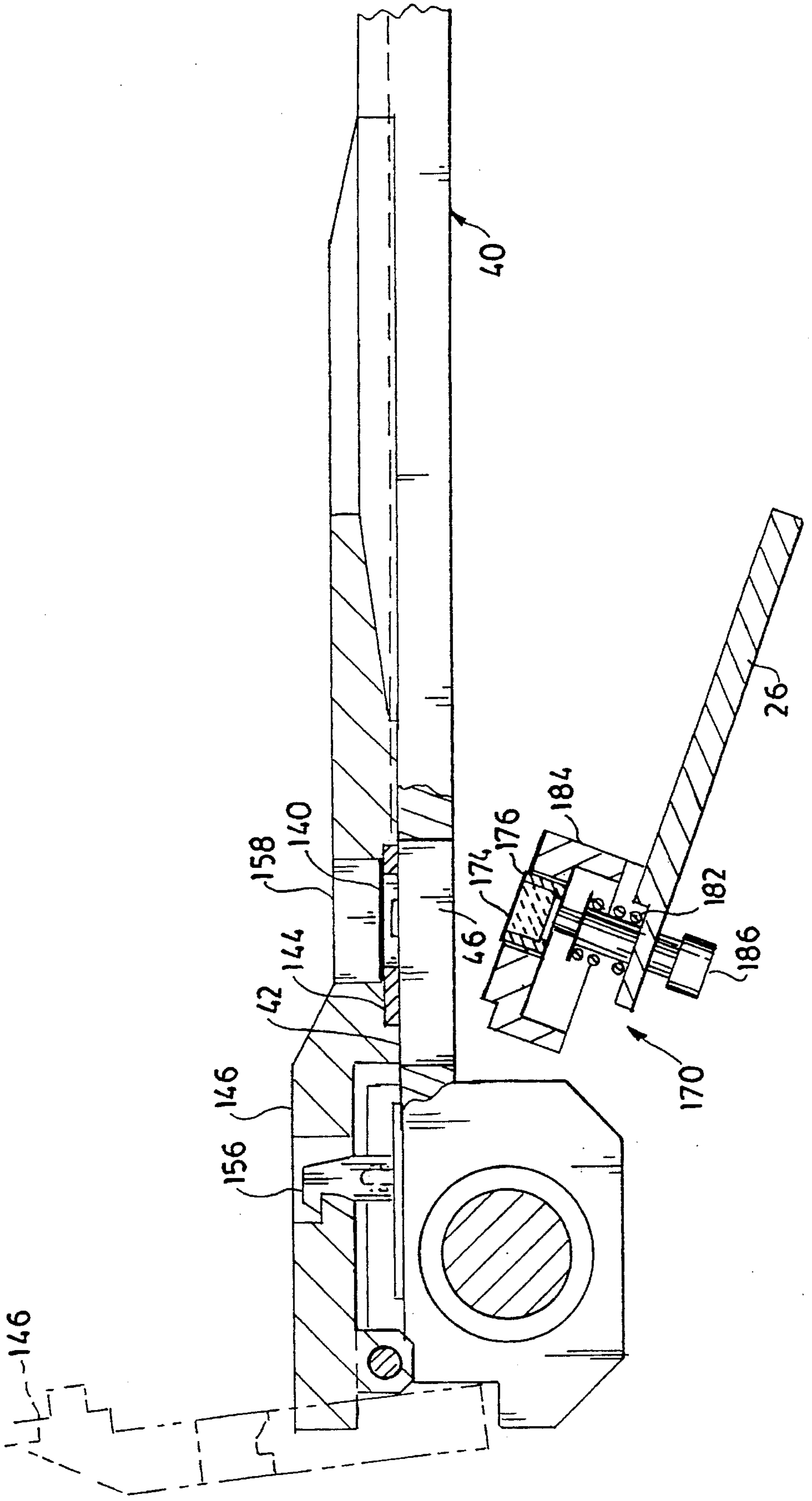
FIG. 8 is a partial side elevational view of the processor of FIG. 7, shown in section, illustrating the engagement of the two heating assemblies after the cover of the processor has been opened.

Turning to FIG. 7 and 8, details of the upper and lower heating assemblies in combination with each other and the remainder of processor 20 will now be described. Adjacent top surface 42 of support plate 40 is a flip-up plate 146 to which upper heating assembly 140; that is, mount fixture 144 and heating element 142, can be mounted via mount holes 147, FIG. 6, configured as shown, and through which threaded fasteners can be inserted. Flip-up plate 146 can be made to selectively open or close by a catch mechanism 156 which engages plate 146. A torsion spring (not shown) holds plate 146 open when catch mechanism 156 is disengaged. An aperture 158 is provided for flip-up plate 146 which is coincident with aperture 150, FIG. 6, when placed in a closed position, FIG. 7.

Turning to the lower heating assembly, button 176 is loosely positioned within a retaining plate 184 which as shown, FIGS. 7 and 8, is mounted to stationary weldment 26.

A series of equally spaced parallel apertures 46, are provided through the thickness of support plate 40, each being sized for receiving a second heating assembly 170 when support plate 40 is moved from loading position (B), to initially inclined position (A). The entire lower heating assembly 170, including stationary weldment 26, is inclined so that the assembly will fit within aperture 46 when support plate 40 is restored to position (A). In a preferable orientation, the exterior surface 188 of retaining plate 184 and top surface 42 are substantially flush to one another when support plate 40 is placed in position (A), while button 176 extends a small distance above top surface 42. The entire lower heating assembly, including retaining plate 184, is thereafter rigid with the exception of button 176 which is movable along axis 190, FIG. 7, due to the resiliency of springs 182 bearing against the bottom of button 176 and weldment 26 respectively.

In operation and referring to FIGS. 1–9, when processor cover 30 is opened, support plate 40 is caused to move from initial inclined position (A) to a substantially horizontal loading position (B) due to the connected interaction between cover 30 and camming means 50, in which cam shaft 52 is rotated, thereby bringing camming surfaces 54 into contact with the bottom of support plate 40. As previously noted, roller arm 28 cannot be engaged while support plate is in position (B).

A plurality of reaction cuvettes 60 can then be loaded on top surface 42 into a series of defined slots (not shown), the compartments of each cuvette 60 facing upward, or oppositely situated away, from top surface 42. Flip-up plate 146 is preferably closed during loading, as shown in FIG. 8. Cuvettes 60 are held loosely on top surface 42, until upper heating assembly 140 is brought into contact therewith. Each cuvette 60 is properly aligned during loading so that the underside of each detection compartment 84 is coincident with a defined aperture 46 to insure alignment with lower heating assembly 170 when support plate 40 is relocated to position (B).

Upper heating assembly 140 is brought into contact with detection compartment 84 by swinging support plate 40 downward so that detection compartment 84 is within aperture 150 and flow passageways 80 on either side of detection compartment 84 are within channel 154. Each flip-up plate 146 is normally locked into place by the engagement of catch 156 which effectively places lower surface 148 in substantial thermal contact with cuvette 60.

Once reaction cuvettes 60 are placed on support plate 40, and upper heating assembly 140 has been positioned as described above, processor cover 30 can be closed, FIG. 7, thereby relocating support plate 40 and reaction cuvettes 60 to initial position (A). This position lowers support plate 40 adjacent stationary weldment 26 and particularly to lower heating assemblies 170. Since the top surface of button 176 preferably extends above support plate top surface 42, the added thickness of each reaction cuvette 60, loads springs 182 thereby placing both upper and lower heating assemblies 140, 170 into compressive and intimate thermal contact with reaction cuvette 60. As noted previously, however, channel 154, FIG. 9, having sufficient clearance for flow passageways 80, however, does not interfere with fluid communication to and from detection compartment 84 while significant thermal contact has been achieved between upper and lower heater assemblies 140, 170, FIG. 6, and cuvettes 60.

Figure 9:
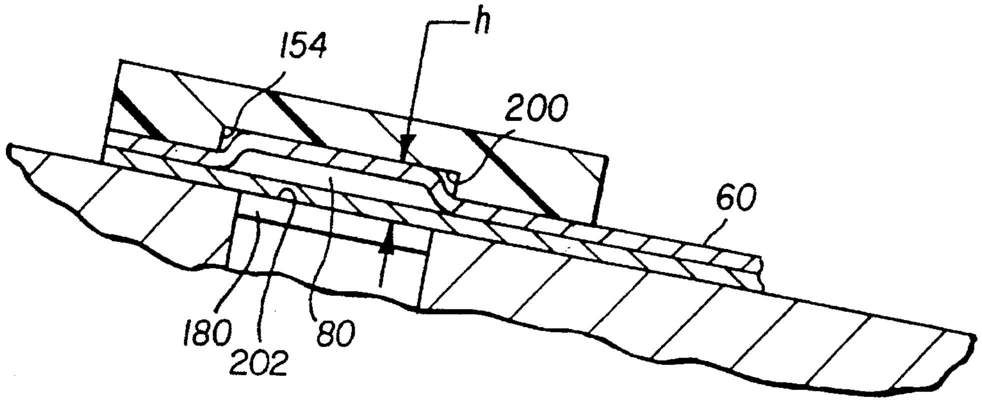
FIG. 9 is an enlarged sectional view of the portion of FIG. 7 identified as IX.

Most preferably, surface 200 of channel 154 is configured and spaced from the surface of window 180, FIG. 9, so that surface 200 acts to constrain the amount of expansion that occurs in compartment 80. As a result, within the range of expected pressures that occur in that compartment, there will be a predicted expansion and volume of flow-through liquid. In addition, flow characteristics at edges 202 of the compartment will be uniform. A useful spacing h between surface 200 and the exterior surface of window 180 to provide this effect is about 0.3 mm.

Figure 10:
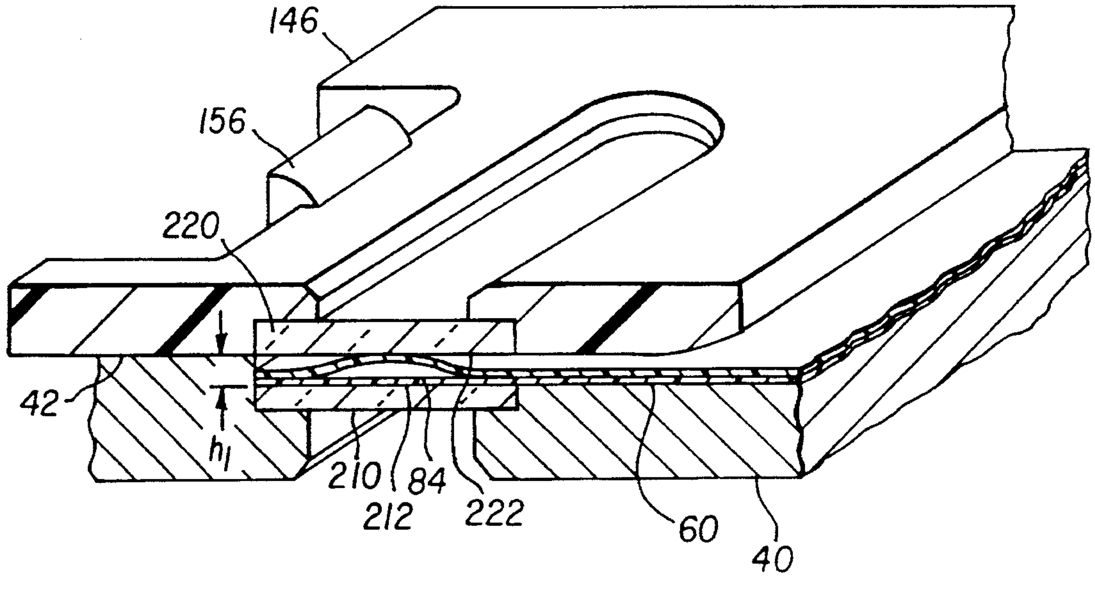
FIG. 10 is a partial side elevational view, shown in section, of an alternate embodiment for engaging and heating a compartment of the reaction cuvette.

Alternately, the upper and lower heating assemblies 140, 170, shown in FIG. 6, can be replaced, see FIG. 10, by providing lower and upper constraint plates 210, 220 positioned in recessed portions which are provided in support plate 40 and flip up plate 146 respectively. Plates 210, 220 are made from a thermally conductive, transparent material, such as glass or sapphire, so that a detection compartment 84 sandwiched between the plates can be optically viewed as previously described. A heating element (not shown) is bonded to each constraint plate 210, 220 in a manner which is conventionally known.

Support plate 40 is milled so that the recessed portion for fitting lower constraint plate 210 defines a predetermined spacing $h_1$ between the top surface 212 of lower constraint plate 210 and the bottom surface 222 of upper constraint plate 220. For a cuvette having wall thicknesses of 0.1 mm, a spacing of 0.3 mm is particularly useful.

In operation, when a cuvette 60 is introduced into the apparatus as shown and fluid is introduced into detection compartment 84, plates 210 and 220 permit an inflation of approximately 0.1 mm before restricting the compartment from further expansion. This allows fluid to pass through the compartment and with a relatively constant flow profile. Because plates 146 and 40 are held in compressive contact by catch mechanism 156, intimate thermal contact is insured between the heat delivering surfaces of plates 210, 220 and detection compartment 84. In this way, both enhanced fluid flow and adequate heating of cuvette 60 are accomplished and without requiring a spring loaded mechanism.

It should be readily apparent that spacing h, can be varied depending largely upon the volume and viscosity of fluid contained within the cuvette, wall thickness and pliability of wall material as well as other determinative factors.

Reading of a color change occurring in any one of the dots in compartment 84, FIG. 2, is done by a reflectometer, which can be conventional (not shown).

In addition, by providing apertures 46, detection compartment 84 can be viewed without having to open cover 30, or by otherwise interrupting the amplification process.

The method of use then of the processing apparatus of the invention will be readily apparent. Fluid flow is forced into compartment 84 by the compression of compartments 62, 64, 66 and 68 in the manner taught by EPA Publication 381,501 noted above, the details of which are expressly incorporated herein by reference. The fluid flow carries first, target nucleic acid, if any exists in the sample, to the circular dots noted in FIG. 2, which are detection sites. Subsequent flow carries reagents for detection. Both flows are done while heat is supplied by the heating surfaces, and the viewing window provided by plates 210, 220, FIG. 10, allows optical viewing of the circular dots during the processing. It can be shown that best results occur when the fluid flow is constrained within predictable boundaries, that is, compartment 84 is kept from expanding to differing values. It is the spacing h of channel 154, FIG. 9, or spacing $h_1$, FIG. 10, which ensures that this will happen. (The shape of compartment 84 is actually flatter when used in the embodiment of FIG. 10, than is actually shown in FIG. 10.)

The invention has been described in detail with particular reference to preferred embodiments thereof, but it will be understood that variations and modifications can be effected within the scope of the invention.

What is claimed is:

1. An assembly for heating a fluid-carrying portion of a reaction cuvette comprising:

a first heating element comprising a source of heat and a heat-delivering surface;

a support for supporting a reaction cuvette having at least one compliant fluid-carrying compartment;

and means for moving said heat-delivering surface into and out of intimate contact with a portion of said supported cuvette, wherein said heat-delivering surface further comprises a) means defining a fixed passage within said heat-delivering surface permanently sized to receive said at least one compliant fluid-carrying compartment for allowing flow therethrough while said first heating element is engaged with said cuvette, and b) means for viewing said fluid-carrying compartment while said first heating element is engaged with said cuvette, said passage extending to said viewing means from opposite sides of said heat-delivering surface.

2. An assembly according to claim 1 wherein said first heating element is made from an optically transparent material.

3. An assembly according to claim 1 further comprising in said assembly a second heating element having a source of heat and a heat-delivering surface, wherein said supported cuvette is positioned between said first and said second heat-delivering surfaces, said assembly further comprising means for moving at least one of said heating elements relative to said reaction cuvette and into and out of engagement therewith.

4. An assembly as claimed in claim 3 further comprising in said assembly means for resiliently biasing said heating elements into contact with said supported cuvette.

5. An assembly as claimed in claim 3 wherein said second heating element is made from an optically transparent material.

6. An assembly as claimed in claim 1 wherein said first heating element is movably connected to said support for moving said heat-delivering surface into and out of contact with said cuvette.

7. An assembly as defined in claim 1, wherein said passage is sized to constrain expansion of said fluid-carrying compartment by pressing against it when fluid pressure is present.

8. A processing apparatus comprising:

a main body having an interior portion;

a cover movably attached to said main body;

a support for supporting a reaction cuvette disposed within said interior portion, said cuvette having at least one compliant fluid-carrying compartment;

a first heating element having a source of heat and a first heat-delivering surface capable of heating said reaction cuvette by contact therewith, said first heating element further comprising a) means defining a fixed passage within said heat-delivering surface permanently sized to receive said fluid-carrying compartment for permitting fluid flow therethrough while said first heating element is in contact with said reaction cuvette; and b) means for viewing said fluid-carrying compartment while said first heating element is engaged with said cuvette, said passage extending to said viewing means from opposite sides of said heat-delivering surface; and means for moving said first heating element into intimate contact with a supported reaction cuvette.

9. A processing apparatus as claimed in claim 8 wherein said first heating element is made from an optically transparent material.

10. A processing apparatus as claimed in claim 8 wherein said support is movable from a first to a second position and is coupled by means to said cover so that said support moves moves from said first position to said second position when said cover is opened.

11. A processing apparatus as claimed in claim 10 further comprising a second heating element having a source of heat and a heat-delivering surface for heating by contact said reaction cuvette.

12. A processing apparatus as claimed in claim 11 further comprising means for resiliently biasing said second heating element so as to compressively contact said cuvette when said support is moved from said second to said first position.

13. A processing apparatus according to claim 11 wherein said second heating element is made from an optically transparent material.

14. A processing apparatus as claimed in claim 10 and further comprising means for moving said first heating element into and out of contact with said reaction cuvette, said means being coupled to said support.

15. A processing apparatus as claimed in claim 8 further comprising means for detecting the presence of at least one substance in said fluid-carrying compartment.

* * * * *

UNITED STATES PATENT AND TRADEMARK OFFICE

CERTIFICATE OF CORRECTION

PATENT NO. : 5,567,617

DATED : October 22, 1996

INVENTOR(S) : Craig A. Caprio, Michael R.Van der Gaag, Charles C.Hinckley, John B. Chemelli It is certified that error appears in the above-indentified patent and that said Letters Patent is hereby corrected as shown below:

Column 10, line 6, after "support", delete --moves--.

Signed and Sealed this

Eighth Day of April, 1997

Attest:

BRUCE LEHMAN

*Attesting Officer*

*Commissioner of Patents and Trademarks*